United States Patent
Bednarek

(10) Patent No.: US 6,693,165 B2
(45) Date of Patent: Feb. 17, 2004

(54) CYCLIC PEPTIDES AS POTENT AND SELECTIVE MELANOCORTIN-4 RECEPTOR ANTAGONISTS

(75) Inventor: Maria A. Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 209 days.

(21) Appl. No.: 09/761,046

(22) Filed: Jan. 16, 2001

(65) Prior Publication Data
US 2002/0016291 A1 Feb. 7, 2002

Related U.S. Application Data
(60) Provisional application No. 60/176,509, filed on Jan. 18, 2000.

(51) Int. Cl.⁷ .................................................. C07K 7/50
(52) U.S. Cl. ........................... 530/317; 514/11; 514/17; 514/18; 530/330
(58) Field of Search ............................ 514/11, 17, 18; 530/317, 330

(56) References Cited

U.S. PATENT DOCUMENTS

| | | | |
|---|---|---|---|
| 4,649,191 A | 3/1987 | Hruby | 530/329 |
| 5,731,408 A | 3/1998 | Hadley et al. | 530/317 |

FOREIGN PATENT DOCUMENTS

| | | |
|---|---|---|
| WO | WO 98/02192 | 1/1998 |
| WO | WO 98/10068 | 3/1998 |
| WO | WO 98/27113 | 6/1998 |
| WO | WO 98/37097 | 8/1998 |
| WO | WO 99/43709 | 9/1999 |
| WO | WO 00/35952 | 6/2000 |
| WO | WO 00/58361 | 10/2000 |

OTHER PUBLICATIONS

Lerner, M., Annals of the New York Academy of Sciences, vol. 885, pp. 153–160.

Schioth, et al., Neuropeptides, vol. 33, No. 3, pp. 191–196, 1999.

Bednarek, et al., "Analogs of MTII, Lactam Derivatives of a–Melanotropin, Modified at the N–Terminus and their Selectivity at Human Melanocortin Receptors 3,4 and 5" Biochem. Bioph. Res. Com. 1999, 261, 209–213.

Sawyer, et al., "4–Norleucine, 7–D–Phenylalanine–a–Melanocyte–Stimulating Hormone: A Highly Potent a–Melanotropin with Ultralong Biological Activity" Proc. Natl. Acad. Sci. USA 1980, 77, 5754–5758.

Kask, et al., "Evidence of involvement of the Melanocortin MC4 Receptor in the Effects of Leptin on Food Intake & Body Weight", Eur. J. Pharmacology 1998, 360, 15–19.

Fan, et al. "Role of Melanocortinergic Neurons in Feeding and the Agouti Obesity Syndrome" Nature 1997, 385, 165–168.

Schioth, et al., "Major Pharacological Distinction of the ACTH Receptor from Other Melanocortin Receptors" Life Sci. 1996, 59, 797–801.

Griffon, et al., "Molecular Cloning, Expression and Characterization of a Fifth Melanocortin Receptor", Biochem. Biophys. Res. Commun. 1994, 200, 1007–1014.

Wessells, et al. "Synthetic Melanotropic Peptide Initiates Erections in Man with Psychogenic Erectile Dysfunction: Double–Blind, Placebo Controlled Crossover Study", J Urology 1998, 160, 389–393.

Wikberg, "Melanocortin Receptors: Perspective for Novel Drugs", Eur. J. Pharmacology 1999, 375, 295–310.

Chen, et al., "exocrine Gland Dysfunction in MC5–R Deficient Mice: Evidence for Coordinated Regulation of Exocrine Function in Melanocortin Peptides", Cell 1997, 91, 789–798.

Kask, et al., "Evidence that Orexigenic Effects of Melanocortin 4 Receptor Antagonist HS014 are Mediated by Neuropeptide", Y. Biochem, Bioph. Res. Commun, 1998, 248, 245–249.

Kask, et al., "Selective Antagonist for the Melanocortin 4 Receptor (HS014) Increases Food Intake in Free–Feeding Rats", Biochem. Bioph. Res. Commun. 1998, 245, 90–93.

Murphy, et al., "Melanocortin Mediated Inhibition of Feeding Behavior in Rats" Neuropeptides 1998, 32, 491–497.

Giraudo, et al., "Feeding Effects of Hypothalamic Injection of Melanocortin 4 Receptor Ligands" Brain Res. 1998, 809, 302–306.

Huszar, et al. "Targeted Disruption of the Melanocortin–4 Receptor Results in Obesity in Mice" Cell 1997, 88, 131–141.

Hruby, et al., Cyclic Lactam a–Melanotropin Analogues of Ac–4–cyclo[Asp5,D–Phe7,Lys10]a Melanocyte–Stimulating Hormone–(4–10)–NH2 with Bulky Aromatic Amino Acids at Position 7 Show Ant. Potency and Selectivity at Specific Malanocortin Receptors J. Med. Chem., 1995, 38, 3454–3461.

Kask, et al., "Discovery of a Novel Superpotent and Selective Melanocortin–4 Receptor Antagonist (HS024): Evaluation in Vitro and in Vivo" Endocrinology, 1998, 139, 5006–5014.

(List continued on next page.)

Primary Examiner—Christopher S. F. Low
Assistant Examiner—David Lukton
(74) Attorney, Agent, or Firm—Mollie M. Yang; David L. Rose

(57) ABSTRACT

Cyclic peptides of formula I are potent and selective antagonists of melanocortin-4 receptors, and as such are useful research tool for the determination of the physiological roles of the MC-4 receptor, as well as for the diagnosis, treatment or prevention of disorders or diseases mediated through the MC-4 receptor.

8 Claims, No Drawings

OTHER PUBLICATIONS

Skuladottir, et al., "Long Term Orexigenic Effect of a Novel Melanocortin 4 Receptor Selective Antagonist" Brit. J. Pharmacology, 1999, 126, 27–34.

Bednarek, et al., "Structure–Function Studies on the Cyclic Peptide MT–II, Lactam Derivative of a–Melanotropin" Peptides 1999, 20, 401–409.

Haskell–Luevano, et al., "Discovery of Prototype Peptidomimetic Agonists at the Human Melanocortin Receptors MC1R and MC4R" J. Med. Chem., 1997, 40, 2133–2139.

Schioth, et al., "Selective Properties of C– and N–terminals and Core Residies of the Melanocyte– Stimulating Hormone on Binding to the Human Melanocortin Receptor Subtypes" Eur. J. Pharm, 1998, 349, 359–366.

Al–Obeidi, et al., Journal of Medicinal Chemistry, vol. 35, No. 1, pp. 118–123, 1992.

CYCLIC PEPTIDES AS POTENT AND SELECTIVE MELANOCORTIN-4 RECEPTOR ANTAGONISTS

CROSS-REFERENCE TO RELATED APPLICATIONS

This application is a non-provisional application related to U.S. Provisional Application Ser. No. 60/176,509 filed on Jan. 18, 2000 priority of which is claimed hereunder

BACKGROUND OF THE INVENTION

Melanocortin peptides or melanotropins, α-MSH, β-MSH, γ-MSH and ACTH, are involved in many physiological functions in vertebrates, mammals and in man. They regulate skin pigmentation and steroid production, modulate immune responses and learning processes, influence energy balance, growth and regeneration of nerves, and several other functions as well.

Five human receptors are known which interact with melanotropins, hMC-1R to hMC-5R. The receptors are seven-helix transmembrane-spanning receptors and belong to the superfamily of G protein-coupled receptors; their activation leads to elevation of cAMP. The melanocortin receptors 1, 3, 4 and 5 recognize α-MSH, β-MSH and γ-MSH, while melanocortin receptor 2 recognizes only ACTH.

Considerable attention has recently focused on melanocortin receptors 3 and 4 that are widely expressed in the central nervous system, and also on melanocortin receptor 5, found in the brain and in various peripheral tissues. The physiological role of hMC-3R and hMC-5R is not well defined, although hMC-5R has recently been implicated in control of lipid and pheromone production in exocrine glands. Rapidly growing pharmacological and genetic evidence suggests that hMC-4R is involved in regulation of the energy balance and body weight in rodents. The role of MC-4R in regulation of food intake and body weight is supported by results obtained from agonist/antagonist administration in rats and from murine genetics. Intraventricular administration of the agonist MTII reduced food intake and conversely, the antagonist SHU9119 increased food intake and body weight. Mice genetically deficient in the melanocortin receptor 4 develop obesity. It could be anticipated therefore that compounds active at MC-4R might be useful in the treatment of eating disorders.

Melanocortin receptor 4 appears to play a role in other physiological functions as well, namely in controlling grooming behavior, erection and blood pressure. The natural hormones, melanotropins, however, have relatively low affinity for hMC3-5R and are not particularly selective. In order to differentiate the physiological role of melanocortin receptor 4 from that of other melanocortin receptors in the brain, in particular from MC-3R, potent and selective antagonists are necessary. The synthetic ligands available at present do not distinguish between the melanocortin receptors. A frequently used research tool is the SHU9119 peptide, a potent antagonist at melanocortin receptors 3 and 4, and an agonist at melanocortin receptor 5. SHU9119 has been extensively studied in vitro and in vivo; injection of this peptide stimulates food intake in rats. A similar lactam derivative, the peptide MTII is a potent but non-selective agonist at hMC3-5R.

Recently several peptides, which are cyclized via disulfide bridges, have been reported as antagonists of the α-MSH responses at MC-3R and MC-4R, and the most potent and MC-4R selective antagonists are HS014, HS024 and HS028. HS014 and HS028 are partial agonists at melanocortin receptors 1 and 5, whereas at the same receptors, HS024 is an antagonist. In rats these antagonists increase food intake and body weight. While SHU9119, HS014, HS024 and HS028 are potent antagonists at MC-4R, they are not sufficiently selective for MC-4R over the other MC receptors. Thus there remains a need to provide for potent and selective antagonists of MC-4R that will allow for the differentiation of the physiological roles of the MC-4 receptor from those of other melanocortin receptors. Such selective antagonists may also be useful as therapeutic agents for the diagnosis, treatment or prevention of diseases and disorders mediated through the MC-4 receptor, more particularly eating disorders related to underweight, cachexia or anorexia of any cause in humans.

SUMMARY OF THE INVENTION

The present invention provides cyclic peptides that are potent and selective antagonists of the human melanocortin-4 receptor. These compounds are useful as research tool for the determination of the physiological roles of the MC-4 receptor, as well as for the diagnosis, treatment or prevention of disorders or diseases mediated through the MC-4 receptor.

DETAILED DESCRIPTION OF THE INVENTION

The present invention provides compounds of the formula I

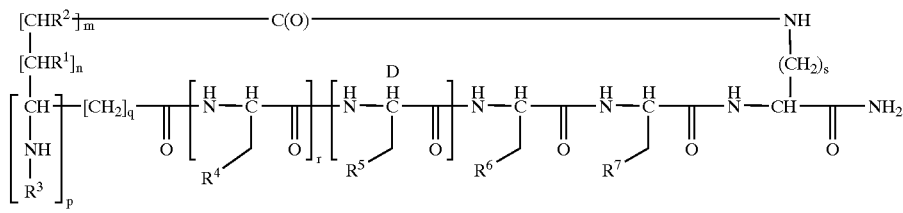

wherein
D represents that the amino acid is an D-amino acid;
m, n, p, q and r are independently 0 or 1, with the proviso that when p is 1, then either q is 1 or n+m is 1, and when p is 0, then q is 0 and m and n are each 1;
s is an integer from 1 to 4;
$R^1$ and $R^2$ are each hydrogen, or $R^1$ and $R^2$ together represent methylene, or $R^1$ and $R^2$ together represent a bond;
$R^3$ is H, Ac, Nle or N—Ac-Nle, with the proviso that when $R^3$ is N—Ac-Nle, r is 0;
$R^4$ is —$(CH_2)_3NH_2$ or 4-imidazolyl;
$R^5$ is selected from 1- or 2-naphthyl, 3-benzothienyl, phenyl optionally substituted with a group selected from halogen, $C_{1-4}$alkyl, and $C_{1-4}$alkoxy;

$R^6$ is —$(CH_2)_2CH_3$, —$(CH_2)_2NHC(=NH)NH_2$ or —$(CH_2)_3NH_2$; and $R^7$ is 3-indolyl, 1- or 2-naphthyl, or phenyl optionally substituted with a halogen; or a salt thereof.

In one embodiment of formula I, r is 0. In another embodiment p and q are each 0. In yet another embodiment s is 3 or 4. In a preferred embodiment, r, p and q are each 0, s is 3 or 4, and m+n is 2.

In another embodiment of formula I, $R^1$ and $R^2$ are each hydrogen.

In another embodiment of formula I, $R^5$ is selected from 2-naphthyl, benzothienyl, and 4-substituted phenyl where said substituent is $C_{1-4}$alkyl, $C_{1-4}$alkoxy or halogen. A subset within this embodiment provides compounds where $R^5$ is selected from 2-naphthyl and 4-substituted phenyl where said substituent is t-butyl, methoxy, chloro, iodo or fluoro.

In yet another embodiment of formula I, $R^6$ is —$(CH_2)_2NHC(=NH)NH_2$.

In another embodiment of formula I, $R^7$ is selected from 3-indolyl, 2-naphthyl and 4-halophenyl. A subset within this embodiment provides compounds where $R^7$ is 3-indolyl.

Compounds of formula Ia represent a subset of formula I:

Ia

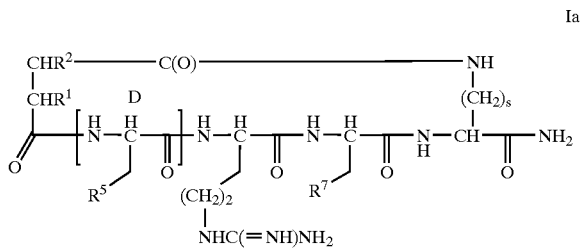

where $R^1$, $R^2$ and s are as defined under formula I; $R^5$ is selected from 2-naphthyl, benzothienyl, and 4-substituted phenyl where said substituent is $C_{1-4}$alkyl, $C_{1-4}$alkoxy or halogen; and $R^7$ is 3-indolyl, 2-naphthyl or 4-halophenyl.

As used in the application, Ac is acetyl, Arg is arginine, His is histidine, D-(2')-Nal is D-3-(2-naphthyl)alanine, Nle is norleucine, Trp is tryptophan. The amino acid components of formula I are L-amino acids unless specified otherwise.

Compounds of the present invention are potent and selective antagonists of the melanocortin-4 receptor, and as such are useful as analytical research tool for the study of the physiological roles of the melanocortin-4 receptor. In addition, compounds of the present invention are useful for the diagnosis, treatment and prevention of diseases and disorders that may benefit from the blocking of the MC-4 receptor, in particular diseases and disorders related to eating disorders.

For analytical and diagnostic purposes the compounds of the present invention can be used in radioactive form, including radioactive labels. In particular the compounds of the invention may be manufactured so as to incorporate radioactive iodine or tritium, or any other suitable radio nuclide. Such a radioactively labeled compound can be used in radioligand binding for the the quantification of specific melanocortin receptors, for the analysis of dissociation constant ($K_i$s or $K_d$s) of drugs competing with specific subtypes of melanocortin receptors, and for the localization of MC-receptors in tissues and tissue sections e.g. by use of receptor autoradiographic techniques. Principles of radioligand binding and receptor autoradiography are well known in the art. As an alternative the compound may be labeled with any other type of label that allows detection of the substance, e.g. a fluorescent label or biotin, and the resulting compound be used for the similar purpose as the radioactively labeled compound.

The compounds of the invention can also be manufactured so as to incorporate a group that can be activated by light, in particular UV-light, the purpose with such activation being to obtain a compound useful for covalent labeling of MC-receptor by use of the photoaffinity labeling technique. Photoaffinity labeling is a technique well known in the art which in the present context is useful for elucidating the structure and topological organisation of the MC-receptors. Thus photoactive derivatives of the compounds of the invention are also part of the present invention. Moreover, preferably photoactive derivates of the compounds of the invention may also be made to incorporate an easily detectable group or label, such as e.g. a radioactive atom, a fluorescent group and/or biotin.

The compounds of the invention can be labeled with gamma and/or positron emitting isotope(s). Such labeled compounds constitute very specific embodiments of the invention and may be administered systematically, or locally, to an animal, preferably a human. These labeled compounds are useful for imaging the in vivo levels and/or localization of MC-receptors by the use of well known techniques among which may be mentioned Scintigraphy, Positron Emission Tomography (PET) and Single Photon Emission Computed Tomography (SPECT). Using such methods information on the distribution and/or quantities of the specific MC-receptors in tissues of the animal or human subject to the investigation is obtained, and such information is of value for diagnosis of disease, in particular functional disturbances in the brain related to MC-receptors.

In addition to analytical and diagnostic utilities, peptides of the present invention may also be used to block the normal physiological response of cells to natural melanotropin (e.g., alpha.-MSH) at the MC-4 receptor. Accordingly, compounds of the present invention may be useful for the prevention and/or treatment of fever, pain, chronic inflammatory diseases, memory disturbances in particular in elderly people, including Alzheimer's disease, nerve regeneration, pathological psychomotor functions of psychiatric conditions such as e.g. catatonic conditions, epilepsy, One aspect of the present invention provides a method for the treatment of eating disorders related to underweight, cachexia or anorexia or bulimia of any cause in humans comprising administering to a person in need of such treatment an effective amount of a compound of formula I. In these conditions the administration of a compound of the invention will increase food intake, which improves the patients' general condition, increases or restores their body weight and prolong their life. In particular the administration of the compound of the invention is beneficial in elderly patients, in cancer patients, and in patients treated with cancer chemotherapeutics, as these patients often suffers from lack of appetite, that often lead to decreased food intake and severe underweight.

Another aspect of the present invention provides a method for growth promotion in an animal which comprises administering to said animal an effective amount of a compound of formula I. In particular growth promotion is desired in animal breeding for meat production such as poultry, pigs and cattle.

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Pharmacologically effective amounts may vary from 0.001 mg/day/kg body weight to 1,000 mg/day/kg body weight. Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally. The effective dosage of active ingredient employed may vary depending on the particular compound employed, the mode of administration, the condition being treated and the severity of the condition being treated. Such dosage may be ascertained readily by a person skilled in the art.

The following examples are provided to illustrate the present invention are are not to be construed as limiting the invention in any manner.

EXAMPLES 1–11
Synthesis of Cyclic Peptides

Elongation of peptidyl chains on p-methoxybenzhydrylamine resin was performed on a 431A ABI peptide synthesizer. Manufacturer-supplied protocols were applied for coupling of the hydroxybenzotriazole esters of amino acids in N-methylpyrrolidone (NMP). The tert-butyloxycarbonyl (Boc) group was used as a semipermanent alpha-amino protecting group, whereas the side chain protecting groups were: tosyl for arginine, benzyloxymethyl for histidine, fluorenylmethyloxy-carbonyl (Fmoc) for lysine, and fluorenylmethyl (Fm) for aspartic acid. Chain building on the synthesizer was concluded by acetylation of the N-terminal residue. The peptidyl resin was transferred into a vessel and Fmoc and Fm groups were manually removed with 20% piperidine in NMP (20 min at room temperature).

For cyclization, the peptidyl resin was thoroughly washed, and then agitated overnight with 5-fold excess of benzotriazole-1-yl-oxy-tris-pyrrolidino-phosphonium hexafluorophosphate (PyBoc) and 6-fold excess of diisopropylethyl-amine in NMP. The procedure was repeated until a negative Kaiser test was observed. The peptidyl resin was washed with NMP and methanol, dried, and treated with liquid hydrogen fluoride in the presence of anisole (or p-cresol) as scavenger (9:1, v/v). After 1 h at 0° C., hydrogen fluoride was removed in vacuo, the resin was washed with ether and extracted with glacial acetic acid, and the extract was lyophylized. The crude peptide was analyzed by analytical reverse-phase high-pressure liquid chromatography (RP HPLC) on a C18 Vydac column attached to a Waters 600E system with authomatic Wisp 712 injector and 991 Photodiode Array detector. A standard gradient system of 0–100% buffer B in 30 min (G1), and, a gradient of 20–80% buffer B in 30 min (G2) was used for analysis: buffer A was 0.1% trifluoroacetic acid in water and buffer B was 0.1% triflouroacetic acid in acetonitrile. HPLC profiles were recorded at 210 nm and 280 nm. Preparative separations were performed on a Waters Delata Prep 40000 system with a semipreparative C18 RP Waters column. The above-described solvent system of water and acetonitrile, in a gradient of 20–80% buffer B in 60 min (G3) was used for separation.

For several compounds [formula I wherein m=n=1, p=q=0], the peptidyl resin was transferred into a vessel, agitated with 6-fold excess of succinic anhydride and 6-fold excess of diisopropylethylamine in N-methylpyrrolidone until a negative Kaiser test was observed, and then thoroughly washed with N-methyl-pyrrolidone and methanol. Subsequent removal of Fmoc group, cyclization, deprotection and cleavage of peptides from a resin, and purification of the crude products were performed as described above.

The chromatographically homogenous compounds were analyzed by amino acid analysis and electrospray mass spectrometry. Correct mass was identified by electrospray mass spectrometry (Hewlett Packard series 1100 MSD spectrometer). Examples of compounds prepared in accordance with the above general procedure and their analytical data are as shown in Tables 1 and 2.

$$\left[CHR^2\right]_m \phantom{xxxx} C(O) \phantom{xxxx} NH$$

(structure with $[CHR^1]_n$, $[CH[CH_2]_q$, NH, $R^3]_p$, $[His]_r$-D-(2')-NaI-Arg-Trp-N—CH—$(CH_2)_s$—$NH_2$)

| Ex. | m | n | p | q | r | s | R¹/R² | R³ | MS-ESI $(M + H)^{2+}$ |
|---|---|---|---|---|---|---|---|---|---|
| 1 | 0 | 0 | 1 | 1 | 1 | 4 | —/— | Ac-Nle | 537.92 |
| 2 | 0 | 1 | 1 | 0 | 1 | 4 | H/— | Ac | 481.3 |
| 3 | 0 | 1 | 1 | 0 | 1 | 4 | H/— | H | 460.3 |
| 4 | 0 | 1 | 1 | 0 | 0 | 4 | H/— | Ac-Nle | 469.3 |
| 5 | 0 | 1 | 1 | 0 | 0 | 4 | H/— | H | 391.7 |
| 6 | 0 | 1 | 1 | 0 | 0 | 4 | H/— | Ac | 412.7 |
| 7 | 1 | 1 | 0 | 0 | 1 | 4 | H/H | — | 452.8 |
| 8 | 1 | 1 | 0 | 0 | 1 | 1 | H/H | — | 431.8 |
| 9 | 1 | 1 | 0 | 0 | 0 | 4 | H/H | — | 384.2 |
| 10 | 1 | 1 | 0 | 0 | 0 | 3 | H/H | — | 377.3 |
| 11a 11b* | 1 | 1 | 0 | 0 | 0 | 4 | $CH_2$ | — | 390.3 & 390.4 |

*two cis isomers separated

EXAMPLE 25

Competitive Binding Assay

The peptides of the present invention were evaluated for antagonist activity in receptor binding assay. Crude membrane preparations were obtained from Chinese hamster ovary cells expressing human MC3, MC4, and MC5 receptors. Cells were rinsed with phosphate-buffered saline (PBS) lacking $CaCl_2$ or $MgCl_2$ (Life Technologies, Gaithersburg, Md., USA), and then detached with enzyme-free dissociation media (Specialty Media, Lavellette, N.J., USA). Cells were pelleted at 2800×g for 10 min and resuspended in membrane buffer (20 mM Tris, pH 7.2, 5 mM ethylenediaminetetraacetic acid) with 5 μg/ml leupeptin, 5 μg/ml aprotinin, 40 μg/ml bacitracin, and 25 μg/ml pefabloc (Boehringer Mannheim). The cells were doused with 10 strokes by using a motor-driven Teflon-coated pestle in a glass homogenizer at low speed. The resulting cell suspension was centrifuged at 4100×g, 4° C., for 20 min. The pellet was resuspended in fresh membrane buffer with protease inhibitors, aliquoted, snap-frozen in liquid nitrogen, and stored at −80° C. The resulting crude membranes were titrated to determine the optimal level necessary for performing binding studies.

Binding reactions (total volume=250 μl) contained MBB (50 mM Tris, pH 7.2, 2 mM $CaCl_2$, 1 mM $MgCl_2$), 0.1% bovine serum albumin, crude membranes prepared from cells expressing human MC3, MC4, or MC5 receptor, 200 pM of [125I]-NDP-α-MSH (Amersham, Arlington Heighs, Ill., USA), and increasing concentrations of unlabeled test compounds dissolved in dimethylsulfoxide (final concentration=2%). Reactions were incubated for 1 h without shaking and then filtered through 96-well filter plates (Packard), presoaked in 1% polyethyleneimine. Filters were washed 3 times with TNE buffer (50 mM Tris, pH 7.4, 5 mM ethylene-diaminetetraacetic acid, 150 mM NaCl), dried and counted by using Microscint-20 in a Topcount scintillation counter (Packard). Nonspecific binding was determined in the presence of 2 μm of unlabeled NDP-α-MSH (Peninsula Laboratories). Binding data were analyzed with GraphPad curve-fitting software (PRISM, San Diego, Calif.) and are presented in the Table below. Active peptides were evaluated in three independent experiments.

TABLE 2

(Structure with $CHR^2$, $CHR^1$, $(CH_2)_3 NH_2$, D, $R^5$, $R^6$, $R^7$, $(CH_2)_s$, $NH_2$)

| Ex. | R¹/R² | R⁵ | R⁷ | MS-ESI $(M + H)^+$ |
|---|---|---|---|---|
| Unless specified, r = 0 and R⁶ is —$(CH_2)_3NHC(=NH)NH_2$ | | | | |
| 12 | Bond | 2-naphthyl | 3-indolyl | 765.4 |
| 13 | H/H | 1-naphthyl | 3-indolyl | 767.5 |
| 14 | H/H | 4-(t-butyl)phenyl | 3-indolyl | 773.5 |
| 15 | H/H | 4-methoxyphenyl | 3-indolyl | 747.4 |
| 16 | H/H | 3-benzothienyl | 3-indolyl | 773.4 |
| 17 | H/H | 4-chlorophenyl | 3-indolyl | 751.3 |
| 18 | H/H | 4-iodophenyl | 3-indolyl | 843.4 |
| 19 | H/H | 4-fluorophenyl | 3-indolyl | 735.4 |
| 20[a] | H/H | 2-naphthyl | 3-indolyl | 739.5 |
| 21[b] | H/H | 2-naphthyl | 3-indolyl | 724.5 |
| 22 | H/H | 2-naphthyl | 4-iodophenyl | 854.3 |
| 23 | H/H | 4-methoxyphenyl | 2-naphthyl | 758.4 |
| 24[c] | H/H | 2-naphthyl | 3-indolyl | 896.4 |

[a] $R^6$ = —$(CH_2)_3NH_2$
[b] $R^6$ = —$(CH_2)_2CH_3$
[c] r = 1

| Ex | hMC-3R | hMC-4R | hMC-5R | 3:4 | 5:4 |
|---|---|---|---|---|---|
| 1 | 32 ± 8 | 0.9 ± 0.1 | 38 ± 1.9 | 35 | 42 |
| 2 | 1 ± 0.4 | 0.1 ± 0.05 | 5.6 ± 1.9 | 10 | 56 |
| 3 | 16 ± 5.2 | 1.7 ± 0.8 | 24 ± 6.7 | 9 | 14 |
| 4 | 22 ± 5.3 | 0.3 ± 0.1 | 28 ± 2.3 | 73 | 93 |
| 5 | 480 ± 140 | 4.3 ± 1.1 | 33 ± 5.1 | 111 | 7 |
| 6 | 220 ± 6.7 | 4.7 ± 0.6 | 1100 ± 150 | 46 | 234 |
| 7 | 52 ± 7.9 | 1 ± 0.1 | 200 ± 3.6 | 52 | 200 |
| 8 | 19 ± 1.5 | 0.2 ± 0.03 | 71 ± 8.4 | 95 | 355 |
| 9 | 150 ± 20 | 0.5 ± 0.2 | 250 ± 72 | 300 | 500 |
| 10 | 63 ± 24 | 0.4 ± 0.2 | 170 ± 89 | 157 | 425 |
| 11 a | 130 ± 16 | 0.6 ± 0.1 | 190 ± 37 | 216 | 316 |
| 11 b | 270 ± 24 | 1.6 ± 0.2 | 540 ± 230 | 168 | 337 |
| 12 | 430 ± 140 | 1.4 ± 0.3 | 380 ± 130 | 300 | 270 |
| 13 | 2600 ± 2000 | 105 ± 9 | 1600 ± 1000 | 25 | 15 |
| 14 | 1500 ± 1100 | 46 ± 6 | 2500 ± 1000 | 37 | 54 |
| 15 | 4700 ± 2500 | 47 ± 5 | 4400 ± 900 | 100 | 94 |
| 16 | 5600 ± 3900 | 69 ± 12 | 3000 ± 1000 | 81 | 44 |
| 17 | 570 ± 290 | 3.5 ± 0.3 | 440 ± 240 | 163 | 126 |
| 18 | 170 ± 87 | 0.9 ± 0.1 | 103 ± 45 | 190 | 114 |
| 19 | 4800 ± 1000 | 70 ± 10 | 10000 ± 2000 | 69 | 143 |
| 20 | 3700 ± 1200 | 44 ± 7 | 2100 ± 500 | 84 | 48 |
| 21 | 6400 ± 2200 | 160 ± 10 | 5000 ± 1700 | 40 | 31 |
| 22 | 120 ± 71 | 0.6 ± 0.1 | 72 ± 43 | 200 | 120 |
| 23 | 650 ± 170 | 4.7 ± 0.2 | 470 ± 150 | 138 | 100 |
| 24 | 3000 ± 1100 | 40 ± 5 | 10000 ± 8700 | 75 | 250 |

EXAMPLE 26 cAMP Assays

Chinese hamster ovary cells expressing a human melanocortin receptor were rinsed with calcium- and magnesium-free PBS (Life Technologies), and detached from the tissue culture flasks by 5-min incubation with enzyme-free dissociation buffer (S-014-B, Specialty Media). Cells were collected by centrifugation and resuspended in Earle's balanced salt solution (Life Technologies) with addition of 10 mM 4-(2-hydroxyethyl)-1-piperazineethanesulfonic acid (Hepes) buffer, pH 7.5, 5 mM MgCl2, 1 mM glutamine, and 1 mg/ml bovine serum albumin to concentration of $1–5 \times 10^6$ cells/ml. Subsequently, cells were counted and the cell suspension was treated with the phosphodiesterase inhibitor 3-isobutyl-1-methylxanthine (to concentration of 0.6 mM).

A test compound was dissolved in dimethyl sulfoxide (DMSO, $10^{-3}$ to $10^{-8}$ M), diluted with buffer, and 0.1 volume of the solution was added to 0.9 volumes of the cell suspension (1 to $5 \times 10^5$ cells); final concentration of DMSO was 1%. After 45 min at room temperature, cells were lysed by incubation at 100° C. for 5 min to release accumulated cAMP. Accumulation of cAMP was measured in an aliquot of the cell lysate with the Amersham (Arlington Heights, Ill.) cAMP detection assay kit (RPA556). The amount of cAMP produced in response to a tested compound was compared to the amount of cAMP produced in response to (α-MSH, defined as a 100% agonist. All active peptides were characterized in three independent experiments.

For assay of functional antagonism the α-MSH dose-response curve was done in the absence and presence of several concentrations of a test compound and cAMP was measured. The test compounds were preincubated 15 min before α-MSH addition.

What is claimed is:

1. A compound having the formula I:

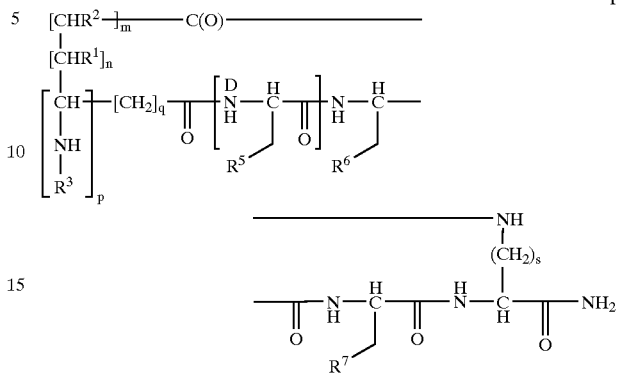

wherein

D represents that the amino acid is an D-amino acid;

m, n, p and q are independently 0 or 1, with the proviso that when p is 1, then either q is 1 or n+m is 1, and when p is 0, then q is 0 and m and n are each 1;

s is an integer from 1 to 4;

$R^1$ and $R^2$ are each hydrogen, or $R^1$ and $R^2$ together represent methylene, or $R^1$ and $R^2$ together represent a bond;

$R^3$ is H, Ac, Nle or N—Ac-Nle;

$R^5$ is selected from 1- or 2-naphthyl, 3-benzothienyl, phenyl optionally substituted with a group selected from halogen, $C_{1-4}$alkyl, and $C_{1-4}$alkoxy;

$R^6$ is —$(CH_2)_2CH_3$, —$(CH_2)_2NHC(=NH)NH_2$ or —$(CH_2)_3NH_2$; and $R^7$ is 3-indolyl, 1- or 2-naphthyl, or phenyl optionally substituted with a halogen; or a salt thereof.

2. A compound of claim 1 wherein p and q are each 0.

3. A compound of claim 1 wherein s is 3 or 4.

4. A compound of claim 1 wherein p and q are each 0, s is 3 or 4, and m+n is 2.

5. A compound of claim 1 wherein $R^1$ and $R^2$ are each hydrogen.

6. A compound of claim 1 having the formula Ia:

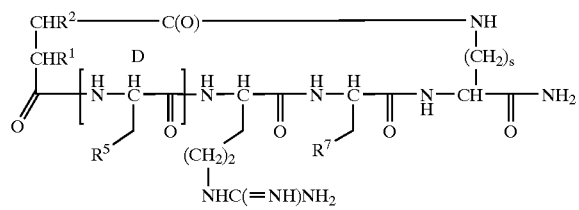

where $R^1$, $R^2$ and s are as defined in claim 1; $R^5$ is selected from 2-naphthyl, benzothienyl, and 4-substituted phenyl where said substituent is $C_{1-4}$alkyl, $C_{1-4}$alkoxy or halogen; and $R^7$ is 3-indolyl, 2-naphthyl or 4-halophenyl.

7. A compound of claim 1 selected from the group consisting of:

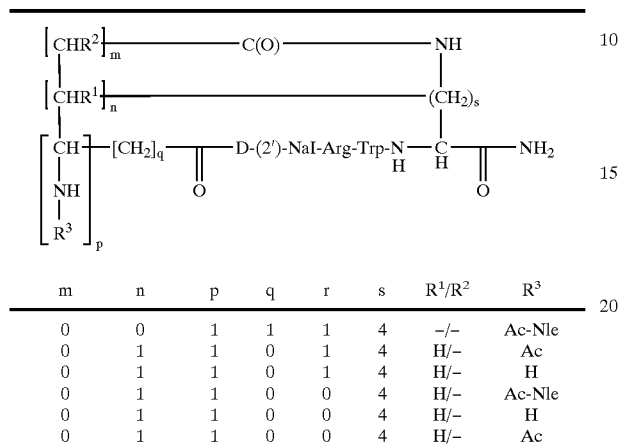

| m | n | p | q | r | s | $R^1/R^2$ | $R^3$ |
|---|---|---|---|---|---|-----------|-------|
| 0 | 0 | 1 | 1 | 1 | 4 | –/– | Ac-Nle |
| 0 | 1 | 1 | 0 | 1 | 4 | H/– | Ac |
| 0 | 1 | 1 | 0 | 1 | 4 | H/– | H |
| 0 | 1 | 1 | 0 | 0 | 4 | H/– | Ac-Nle |
| 0 | 1 | 1 | 0 | 0 | 4 | H/– | H |
| 0 | 1 | 1 | 0 | 0 | 4 | H/– | Ac |

-continued

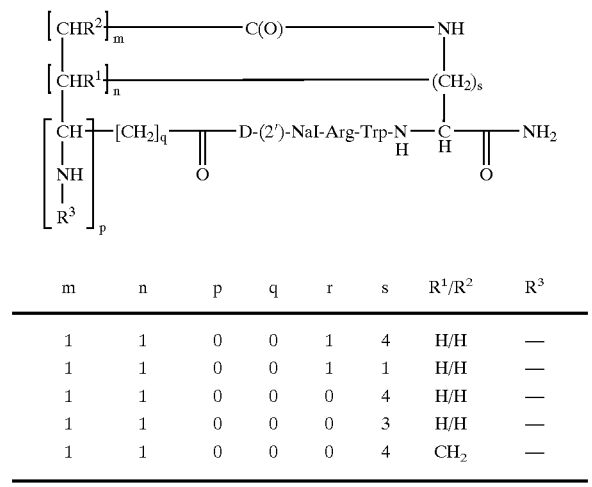

| m | n | p | q | r | s | $R^1/R^2$ | $R^3$ |
|---|---|---|---|---|---|-----------|-------|
| 1 | 1 | 0 | 0 | 1 | 4 | H/H | — |
| 1 | 1 | 0 | 0 | 1 | 1 | H/H | — |
| 1 | 1 | 0 | 0 | 0 | 4 | H/H | — |
| 1 | 1 | 0 | 0 | 0 | 3 | H/H | — |
| 1 | 1 | 0 | 0 | 0 | 4 | $CH_2$ | — |

8. A compound of claim 1 selected from the group consisting of

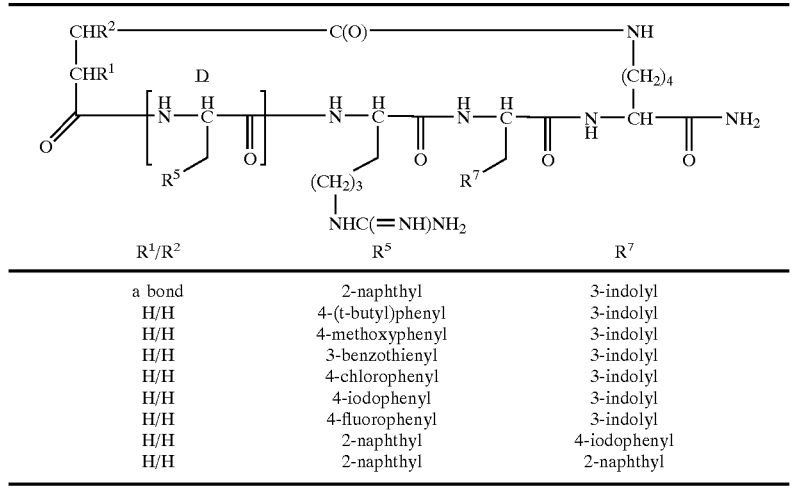

| $R^1/R^2$ | $R^5$ | $R^7$ |
|-----------|-------|-------|
| a bond | 2-naphthyl | 3-indolyl |
| H/H | 4-(t-butyl)phenyl | 3-indolyl |
| H/H | 4-methoxyphenyl | 3-indolyl |
| H/H | 3-benzothienyl | 3-indolyl |
| H/H | 4-chlorophenyl | 3-indolyl |
| H/H | 4-iodophenyl | 3-indolyl |
| H/H | 4-fluorophenyl | 3-indolyl |
| H/H | 2-naphthyl | 4-iodophenyl |
| H/H | 2-naphthyl | 2-naphthyl |

\* \* \* \* \*

UNITED STATES PATENT AND TRADEMARK OFFICE
CERTIFICATE OF CORRECTION

PATENT NO. : 6,693,165 B2
DATED : February 17, 2004
INVENTOR(S) : Maria A. Bednarek It is certified that error appears in the above-identified patent and that said Letters Patent is hereby corrected as shown below:

Column 11,
Lines 19 through 26, the table should read -- not contain the column listed as "r" --.

Column 12,
Lines 14 through 21, the table should read -- not contain the column listed as "r" --.

Signed and Sealed this

Thirteenth Day of July, 2004

JON W. DUDAS
*Acting Director of the United States Patent and Trademark Office*